US011779538B2

(12) United States Patent
Noe et al.

(10) Patent No.: US 11,779,538 B2
(45) Date of Patent: *Oct. 10, 2023

(54) EMULSIONS FOR TREATING MUCOUS MEMBRANE INFECTIONS

(71) Applicant: ProFem GmbH, Vienna (AT)

(72) Inventors: Marion Noe, Vienna (AT); Christian R. Noe, Vienna (AT)

(73) Assignee: ProFem GmbH, Vienna (AT)

( * ) Notice: Subject to any disclaimer, the term of this patent is extended or adjusted under 35 U.S.C. 154(b) by 0 days.

This patent is subject to a terminal disclaimer.

(21) Appl. No.: 16/763,372

(22) PCT Filed: Nov. 14, 2018

(86) PCT No.: PCT/EP2018/081253
§ 371 (c)(1),
(2) Date: May 12, 2020

(87) PCT Pub. No.: WO2019/096857
PCT Pub. Date: May 23, 2019

(65) Prior Publication Data
US 2020/0281852 A1   Sep. 10, 2020

(30) Foreign Application Priority Data

Nov. 14, 2017  (EP) ...................................... 17201650
Nov. 14, 2017  (EP) ...................................... 17201651

(51) Int. Cl.
| A61K 9/10 | (2006.01) |
| A61K 9/107 | (2006.01) |
| A61P 15/02 | (2006.01) |
| A61P 31/04 | (2006.01) |
| A61K 31/196 | (2006.01) |
| A61K 31/4174 | (2006.01) |
| A61K 47/22 | (2006.01) |
| A61K 9/00 | (2006.01) |
| A61K 9/06 | (2006.01) |
| A61K 45/06 | (2006.01) |

(52) U.S. Cl.
CPC .............. *A61K 9/107* (2013.01); *A61K 9/10* (2013.01); *A61K 31/196* (2013.01); *A61K 31/4174* (2013.01); *A61K 47/22* (2013.01); *A61P 15/02* (2018.01); *A61P 31/04* (2018.01); *A61K 9/0014* (2013.01); *A61K 9/0034* (2013.01); *A61K 9/06* (2013.01); *A61K 45/06* (2013.01)

(58) Field of Classification Search
CPC .......... A61P 15/02; A61P 31/04; A61K 9/107; A61K 31/196; A61K 9/10; A61K 31/4174; A61K 47/22; A61K 9/0014; A61K 9/06; A61K 45/06; A61K 9/0034
See application file for complete search history.

(56) References Cited

U.S. PATENT DOCUMENTS

| 5,686,089 A | 11/1997 | Mitra et al. |
| 2004/0101538 A1* | 5/2004 | Larnier ................. A61K 45/06 424/400 |
| 2007/0292355 A1 | 12/2007 | Tamarkin et al. |
| 2009/0208558 A1 | 8/2009 | Noe et al. |
| 2010/0256238 A1* | 10/2010 | Tanoue ................ A61K 31/192 514/567 |
| 2014/0030312 A1 | 1/2014 | Noe et al. |
| 2016/0120797 A1 | 5/2016 | Rayudu |
| 2020/0281853 A1* | 9/2020 | Noe ....................... A61K 47/22 |

FOREIGN PATENT DOCUMENTS

| CL | 206202466 | 9/2003 |
| CL | 200502930 | 8/2006 |
| CL | 202001273 | 10/2020 |
| EP | 0 923 937 A2 | 6/1999 |
| WO | WO 02/078648 A2 | 10/2002 |
| WO | WO 2007/131253 A2 | 11/2007 |

OTHER PUBLICATIONS

International Search Report dated Feb. 12, 2019, in PCT/EP2018/081253, 3 pages.
Mendling, W. et al., "Use of locally delivered dequalinium chloride in the treatment of vaginal infections: a review", Archives of Gynecology and Obstetrics, vol. 293, No. 3, Oct. 27, 2015, pp. 469-484.
European Office Action dated May 29, 2018, in Patent Application No. 17201650.3, 13 pages.
European Office Action dated Jun. 1, 2018, in Patent Application No. 17201651.1, 13 pages.
Indian Office Action dated Nov. 10, 2021 in Indian Patent Application No. 202037023811, 7 pages.
Chilean Office Action dated Aug. 12, 2021 in Chiliean Patent Application No. 202001272 (with English translation), 17 pages.
Notification of Reasons for Refusal dated Oct. 25, 2022, in Japanese Patent Application No. 2020-544154, (with English-language Translation).
Office Action dated Jan. 12, 2023, in Chinese Patent Application No. 201880085721.3 (with English-language Translation).

* cited by examiner

*Primary Examiner* — Sean M Basquill
(74) *Attorney, Agent, or Firm* — Oblon, McClelland, Maier & Neustadt, L.L.P.

(57) ABSTRACT

The invention relates to an emulsion, e.g. in the form of a salve or a cream, with an aqueous phase and an oil phase, containing an NSAID, characterised in that: (a) the NSAID in the aqueous phase is in a concentration range that corresponds to half to a tenth of the standard concentration for these active substances; (b) the weight ratio of the water-to-oil phase in said emulsion is between the values 2.0 and 2.7; and (c) the pH value of the emulsion is not below the value 6.5 and not above 8.5, preferably in the region of between 7.0 and 8.0, particularly for application in the topical treatment of vaginal fungal infections.

20 Claims, 1 Drawing Sheet

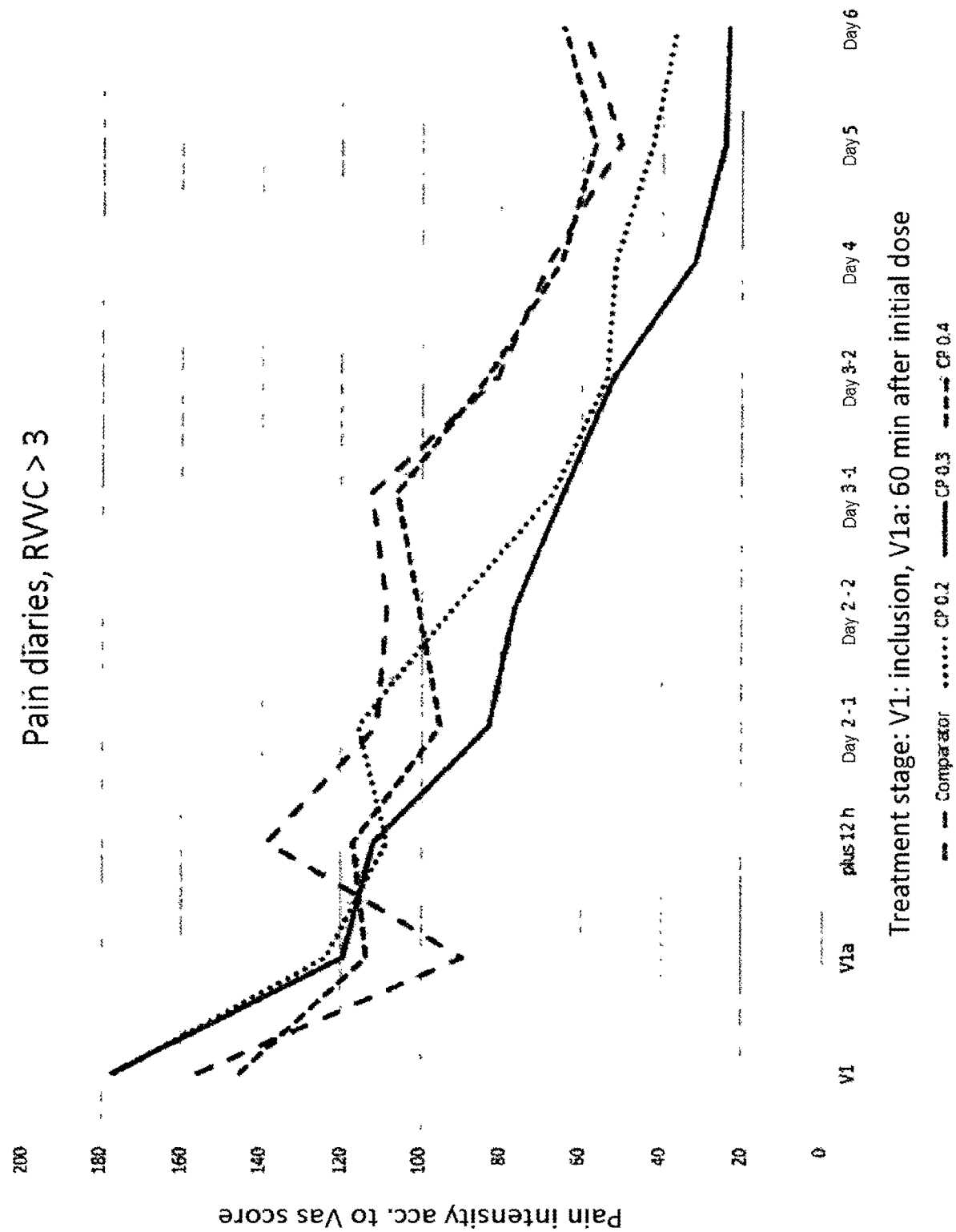

EMULSIONS FOR TREATING MUCOUS MEMBRANE INFECTIONS

The invention relates to emulsions for treating mucosal infections, in particular inflammatory vaginal infections.

WO 2007/131253 A2 relates to the use of an antimycotic active substance and an epithelial or endothelial cell adhesion inhibitor for producing a combined medicament for the topical treatment of Candida mycoses selected from vulvovaginal candidiasis, oropharyngeal candidiasis (oral thrush), nappy dermatitis (nappy rash) and intertriginous eczema.

WO 02/0768648 A2 relates to pharmaceutical compositions for topical application containing an antimycotic, for example terbinafine, and a second active substance, for example diclofenac or indomethacin. The compositions may be used for the prevention or treatment of fungal infections, particularly those caused by dermatophytes.

U.S. Pat. No. 5,686,089 A relates to pharmaceutical compositions for topical application containing an antimicrobial active substance and a moisturising component. The compositions can be used for example for vaginal fungal infections.

Mendling et al. (Mendling, Werner, et al. "Use of locally delivered dequalinium chloride in the treatment of vaginal infections: a review." Archives of gynecology and obstetrics 293.3 (2016): 469-484) describes possibilities for treating vaginal infections with dequalinium chloride.

The object of the present invention is to provide improved NSAID preparations which are particularly suitable for the treatment of mucosal infections and inflammation. In particular, the object of the invention to provide combination preparations of an antimycotic and an NSAID which are particularly well suited for the topical treatment of vaginal and dermal fungal infections. Such emulsions should also be effective for stubborn fungal infections, which occur particularly in the vaginal area, and should be microbiologically and chemically stable.

Accordingly, the present invention relates to an emulsion, preferably in the form of a salve or a cream, comprising an aqueous phase and an oil phase (fatty phase), containing an NSAID, characterised in that (a) the NSAID in the aqueous phase is in a concentration range that corresponds to half to a tenth of the standard concentration for these active substances in other formulations, with respect to the single dose, in that (b) the weight ratio of the aqueous phase to the oil phase in said emulsion is between 2.0 and 2.7, and in that (c) the pH value of the emulsion is not below the value 6.5 and not above 8.5, preferably in the range of 7.0 to 8.0, preferably for the treatment of mucosal infections and mucosal inflammation, in particular for use in the topical treatment of mucosal infections and mucosal inflammation.

In addition, the present invention relates to an emulsion, preferably in the form of a salve or a cream, comprising an aqueous phase and an oil phase (fatty phase), containing an antimycotic and an NSAID, characterised in that (a) the NSAID is present in the aqueous phase in a concentration range that corresponds to half to a tenth of the standard concentration for these active substances in other formulations, with respect to the single dose, in that (b) the weight ratio of the aqueous phase to the oily phase in this emulsion is between 2.0 and 2.7, and in that (c) the pH value of the emulsion is not less than the value 6.5 and not more than 8.5, preferably in the range of 7.0 to 8.0, preferably for the treatment of dermal and vaginal fungal infections, in particular for use in the topical treatment of vaginal fungal infections.

The present invention provides improved preparations of the kind described in the introduction. In particular, the preparations according to the invention show not only optimised pharmacokinetics by attacking directly at the site of infection, but also optimal pharmacodynamics. The preparations according to the invention allow a sufficient efficacy of the NSAIDs when used at low concentrations—and thus with few side effects. In the case of the combination preparations according to the invention, this not only enables a particularly good efficacy of the antimycotic, but also significantly improves the interaction with the NSAID by ensuring sufficient efficacy through a low concentration of NSAID without having to accept the side effects (irritation, burning, etc.) that may occur. In practice, this leads to the fact that combinations of antimycotic and NSAID, which were previously not usable for these reasons relating to side effects, can be made available to patients with the teaching of the present invention and these patients can now be provided with a successful therapy. According to the invention, however, it has been shown that the concentration of the NSAID in the aqueous phase is of decisive importance for an optimal pharmacodynamic effect. The availability of the introduced NSAID is achieved by the interaction of the preparation process, the water/oil ratio and the pH value, which ensures the predominant presence of the NSAID in its salt form.

The preferred NSAIDs used in accordance with the invention are selected from the group consisting of diclofenac, bufexamac, ibuprofen, dexibuprofen, ketoprofen, flurbiprofen, piroxicam, meloxicam, lornoxicam, flufenamic acid, mefenamic acid, naproxen and indometacin. The standard concentration of diclofenac used in medicaments approved for topical therapy is in the range of 1 to 2% (10 mg/g or 20 mg/g). According to the invention, diclofenac is used in a concentration of 0.1% to 0.5% (1-5 mg per g cream), preferably from 0.2% to 0.35%. The usual concentration in medicaments approved for topical therapy in which ibuprofen is used is 5% (50 mg/g cream/gel). According to the invention, ibuprofen is used in a preferred amount of 0.5 to 2.5% (5-25 mg per g cream), preferably from 1 to 2%. Further examples of preferred NSAIDs and their preferred amounts ("concentration according to the invention") in relation to the 'standard' doses can be found in Table A.

TABLE A

| Active substance | Individual dose | Daily maximum dose oral/i.v. | Example | Individual dose | Daily maximum dose topical | Example | Concentration according to the invention |
|---|---|---|---|---|---|---|---|
| Diclofenac sodium | 50-75 mg | 150-225 mg | Voltaren 50 mg tablets 75 mg amp. | 40-80 mg | 240 mg | Voltadol pain relief gel 1%, 10 mg/g 2%, 20 mg/g | 0.2-0.5 wt. % |

TABLE A-continued

| Active substance | Individual dose | Daily maximum dose oral/i.v. | Example | Individual dose | Daily maximum dose topical | Example | Concentration according to the invention |
|---|---|---|---|---|---|---|---|
| Indometacin | 25-75 mg | 50-150 mg | Indocid 25 mg 75 mg ret. | 20-40 mg | 40-80 mg | IndometGel 1%, 10 mg/g | 0.1-0.4 wt. % |
| Naproxen | 250-500 mg | 1000 mg | Naproxen FT 250/500 mg Naproxen Susp. 50 mg/ml | | | | 0.5-2.5 wt. % |
| Ibuprofen | 200-800 mg | 2400 mg | Ibuprofen FT 200/400/800 mg | 100-250 mg | 1000 mg | Ibutrop cream/gel 5%, 5 g/100 g | 0.5-2.5 wt. % |

In the context of the invention, the following NSAIDs are particularly preferred:

| NSAID | Preferred concentration (wt. %) | Preferred individual dose (mg) |
|---|---|---|
| Diclofenac | 0.1-0.5 (preferably 0.2-0.4) | 4 to 8 mg |
| Indometacin | 0.1-0.4 | 2-8 mg |
| Naproxen | 1-5 | 20 to 100 mg |
| Ibuprofen | 0.5-2.5 | 10 to 50 mg |
| Dexibuprofen | 0.25-1.25 | 5 to 25 mg |
| Ketoprofen | 0.25-1.25 | 5 to 25 mg |
| Mefenamic acid | 0.5-4 | 10-40 mg |
| Lornoxicam | 0.02-0.04 | 0.4 to 0.8 mg |

According to the invention, it has been shown that the treatment of fungal diseases, in particular *Candida mycoses*, can be carried out particularly effectively with the aid of a combination preparation of an antimycotic with a drug which at the same time influences the adhesion of the microorganisms. The medicaments are advantageously applied topically, because the site of action is thus directly reached and at the same time a minimal systemic burden is caused. Such active substance combinations are protected by patents derived from WO 2007/131253 A2.

The subject of the invention relates to drug combinations particularly suitable for vaginal application, as well as their preparation and use. By taking into account the special physiological and pathophysiological conditions in the vagina, both a special composition and a special preparation process have proven to be particularly advantageous. Observing specific parameters leads to a particularly good therapeutic effect in the treatment of vaginal infections.

With regard to the adhesion-inhibiting component, the present compound only relates to the group of NSAIDs (non-steroidal anti-inflammatory drugs), because drugs in this group have an analgesic and anti-inflammatory effect in addition to the anti-adhesive effect, which prevents adhesion. Both effects, especially the anti-inflammatory effect, are particularly welcome in recurrent forms of *Candida mycosis* because they are associated with chronic inflammation and severe pain.

Preferred NSAIDs are diclofenac, ibuprofen, dexibuprofen, ketoprofen, flurbiprofen, mefenamic acid, naproxen, lornoxicam and indometacin. Preferred antimycotics are nystatin, ciclopirox or ciclopiroxolamine, or antimycotics from the group of azoles (imidazoles, triazoles, tetraazoles) such as clotrimazole, fluconazole, miconazole, itraconazole, tioconazole, voriconazole, bifonazole, econazole, isoconazole, fenticonazole, sertaconazole, ketoconazole, posaconazole, quilseconazole, oteseconazole (VT-1161), from Ibrexafungerp (SCY-078).

Structural Formula of Ibrexafungerp (SCY-078)

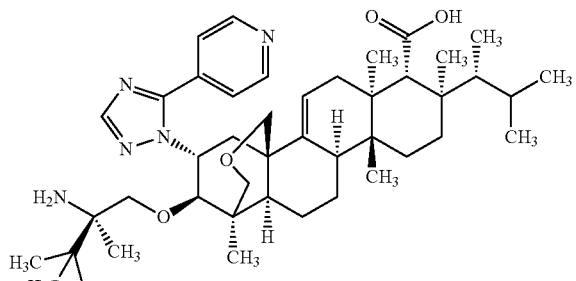

Structural Formula of Oteseconazole (VT-1161)

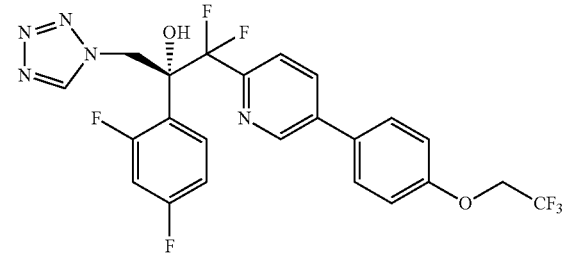 [SMILES: O[C@@](Cn1cnnn1)(c1ccc(F)cc1F)C(F)(F)c1ccc(-c2ccc(OCC(F)(F)F)cc2)cn1]

Surprisingly, it has been shown during the application that in order to achieve an optimal effect, the ratio of the proportions of the antimycotic and of the NSAID is of particular importance. In the combinations of an antimycotic with an NSAID, the antimycotic can be used in standard dosages (clotrimazole 1-10%, ketoconazole 1-5%, preferably 2%, nystatin 100,000 IE/ml or g). Since the NSAID exerts its effect in the same way on the pathogen in the vagina and on the vaginal epithelium, on the one hand the topical application of the medicament, where it is applied directly at the site of action, is clearly superior to a systemic application, and on the other hand the NSAID should therefore be used in much lower doses than in the standard systemic applications as an analgesic. In vaginal application a therapeutic effect is already achieved from one tenth, preferably one fifth of a concentration of the active substance which is used in standard dermal formulations of NSAIDs (in the case of diclofenac 200 to 500 mg/100 g salve). The low concentration of the active substance is also therefore particularly advantageous because the systemic uptake of the NSAID is negligible and there is no risk of systemic side effects. At the same time it has to be taken into account that the topical application on mucosas may easily lead to an overdose of the NSAID (for example a cream with diclofenac: from 0.5% is painful and the rapid pain relief effect does not occur any more). The application of NSAID-containing creams that are available on the market (1-2% diclofenac, 5% ibuprofen) to mucosas is warned against by the various instructions for use (for example instructions for use for voltaren emulgel, ibutop-gel), because the mucosas will be irritated, which counteracts the anti-inflammatory effect. Therefore, according to the invention, the NSAID should not be used in a quantity greater than 50% of the standard lowest formulation for dermal applications. Irritations can occur already at this concentration. Thus, the active substance concentration of the NSAID to be used preferably moves within a relatively small therapeutic window of 10-60, preferably of 20-40% of the value that is usual for topical formulations. Accordingly, a particularly preferred emulsion according to the present invention contains diclofenac as NSAID, with diclofenac being contained in a concentration range of 0.2-0.4 percent by weight of the emulsion. It is even more preferred if diclofenac is present in a concentration range of 0.2-0.35 percent by weight of the emulsion. Most preferred is a concentration range of 0.25-0.35 weight percent. Higher proportions of lower alcohols, such as ethanol or isopropanol (>10%), increase the irritant effect and therefore counteract the pain- and inflammation-relieving effects.

It is known that finding a dosage form for topical application in the vagina is made difficult by the fact that the medicament can easily leak during application, which makes reliable dosing difficult and prevents sufficient exposure time. In view of the relatively narrow therapeutic window, drugs according to the present invention presuppose, in order to achieve the desired therapeutic effect, that the active substance, above all the NSAID component, remains safely at the site of action. For this reason, the ratio of the oil phase containing the antimycotic to the water phase containing the NSAID in the medicament is within a relatively narrow range. Solutions, emulsions or gels with a high water and/or alcohol content are to be excluded as dosage forms according to the present invention because an uncontrolled loss by leakage from the vagina is to be expected.

Semi-solid emulsions (oil-in-water or water-in-oil), preferably in the form of a cream, are particularly well suited to bring the active substances efficiently and in a concentrated form to surfaces with biofilms. The viscosity of the emulsions is strongly determined by the water-to-oil ratio. Surprisingly it has been found that the water-to-oil ratio is of special importance in the formulation of the emulsion. A higher proportion of fat components hinders the development of the efficacy. By contrast, a lower fat proportion leads to a stronger irritating effect. To achieve an optimal therapeutic effect, the water-to-oil ratio should not exceed a value of 2.7. Above this level, the active substance is flushed out too quickly with the vaginal secretion, which means that there is not enough time to exert its adhesion-suppressing effect on the outer layer of the vaginal epithelium to which the fungus adheres. (The active substance, which is washed out very quickly when the water-to-oil ratio is too high, may at best additionally also cause an irritating effect as a side effect).

Surprisingly, it has been found that chronic fungal diseases of the vagina are often not caused by a stronger resistance of the pathogens, but rather by a simultaneous chronic inflammation of the vaginal epithelium, which is initially caused by the infection. In such chronic cases, a cure can only be achieved if it is ensured that the NSAID remains in the vagina.

In the same way as too much water in the emulsion has a negative effect, too much fat should also be avoided. In view of the low concentration in which the NSAID is used, it is of particular importance, in order to achieve the therapeutic effect, that the release of the active substance at the site of action is rapid and not protracted. A slow release, such as from the oily phase, does not guarantee that the required therapeutic concentration is achieved at the site of action. For this reason, the water-to-oil weight ratio in the emulsion should not fall below 2.0. Consequently, the value of the water-to-oil weight ratio of the emulsions according to the invention also has a window between 2.0 and 2.7, preferably between 2.1 and 2.6, even more preferably between 2.2 and 2.55.

It is essential that the NSAIDs are in salt form (or ionic form) in accordance with the invention, both during incorporation and during use. Therefore, their incorporation into the formulation is important. When the NSAID is incorporated in its free form or when it is incorporated as a salt into the oily phase, the therapeutic effect is massively impaired. Whereas the antimycotic is preferably incorporated into the oily phase and is present therein, the method according to the invention therefore generally involves the NSAID being introduced into the aqueous phase before the emulsion is prepared. Alternatively, the solid salt of the NSAID can be incorporated into the (largely) finished emulsion in finely crystalline or micronised form, or as a hydrogel.

A rapid release is ensured if the active substance is present in the aqueous phase of the emulsion, which presupposes that the NSAID is present as a salt. Most NSAIDs are weak acids with a pKa value of 4-5 (diclofenac 4.15, ibuprofen 4.91, mefenamic acid 4.2, indometacin 4.5, naproxen 4.2). Accordingly, they are already present in the weakly acidic environment partly in free form, and are thus extracted into the oil phase, which may lead to a reduced effect or loss of effect. Since with decreasing pH value the active substance proportion of the NSAID present as free acid increases in the oil phase, a pH value of at least pH=6 is appropriate in order to have a therapeutic effect in the drugs at the active substance concentrations according to the invention.

Preferably, the emulsion according to the invention is suitable for vaginal application. Unsuitable for vaginal application are, for example, compositions which have a high content of mucosa-damaging substances, for example ethanol or isopropanol. It is therefore preferred that the emulsion according to the invention does not contain more than 10 wt. %, in particular not more than 5 wt. %, of ethanol. It is also preferred that the emulsion according to the invention does not contain more than 15 wt. %, in particular not more than 7.5 wt. %, of isopropanol.

The combination of a lipophilic antimycotic, of the structural type of clotrimazole, with the weak acids of the NSAIDs also means that the combination is only stable within a relatively narrow pH window. Below a pH of 6, clotrimazole becomes unstable, whereas with NSAIDs there may be a decrease in chemical stability in the alkaline environment (in the case of diclofenac from pH 8.00-8.5). The chemical stability is additionally influenced in turn by the water-to-oil ratio and the proportion of alcoholic substances. In combination drugs of azoles and the acidic NSAIDs, unfavourable stability conditions arise from the direct reactivity of the active substances. It should also be noted that the pH value of an emulsion influences the fundamental physiological compatibility. For this reason, relatively narrow limits are also set with regard to the pH value of the formulation. According to the invention, the (aqueous phase of the emulsion) has a pH value in the range of 6.5 to 8.5, preferably 7-8.

Since the introduction of the NSAID salt into an antimycotic drug makes the pH value more alkaline, the preservative usually used in comparable emulsions containing only clotrimazole is not always sufficiently effective. The semi-solid antimycotic drugs according to the present invention are therefore preferably protected against microbial attack with such preservatives and antiseptics which are effective in the pH range of the emulsion. In drugs according to the invention, which are used for the treatment of a solely fungal infection, the content of the antiseptic is kept low in an appropriate manner so as not to impair the normal vaginal flora. The biofilms formed by the growth of fungi often contain not only fungi but also other pathogenic microorganisms. Just by increasing the concentration of the antiseptic accordingly, even such mixed infections can be detected therapeutically. Therefore, the addition of a higher amount of an antiseptic, sufficient for an acute antimicrobial effect, to the claimed drugs constitutes a further subject of the invention. Preferred antiseptics are quaternary ammonium salts, such as benzalkonium chloride, and dequalinium chloride, as well as phenoxyethanol. Preferred concentrations are at least 0.2 weight percent for benzalkonium chloride, at least 0.2 weight percent for dequalinium chloride, and at least 2 weight percent for phenoxyethanol.

Among the bacterial microorganisms found in the vaginal biofilms, typical intestinal germs such as *Enterobacter, E. coli* and/or for example *Klebsiella pneumoniae* as well as anaerobes such as *Gardnerella vaginalis* and *Prevotella* spp. play a particular role. These are also covered by the claimed antiseptics, but in proven cases of such an infection, it is advisable to use an antibiotic active against anaerobes instead of or in addition to the antiseptic. Therefore, the addition of an antibiotic which is effective against anaerobic germs constitutes a further subject of the invention. Preferred antibiotics are phosphomycin, clindamycin, metronidazole, nitrofurantoin, nitrofurazone, nitrofurantoin, nifuratel, nifuroxacin, nitroxolin, trimethoprim, sulfadiazine and cotrimoxazole.

Decisive for breaking up the biofilm is the presence of an NSAID in the described concentrations and conditions in an emulsion in the described composition and described proportions.

Mucosal surfaces offer ideal conditions for the formation of biofilms, which are particularly resistant to therapy. By influencing the moist, physiologically acidic environment of the vagina, the vaginal microbiome makes a decisive contribution to the efficacy of topically applied dosage forms, since the availability of the drugs is pH-dependent. These conditions are one of the contributory causes that the currently marketed topical antimycotics have only a very limited success in the therapy of chronic vulvovaginitis, especially in case of mixed infections with bacteria. The composition of the drug combinations according to the invention is, in the described combinations, particularly suitable for the treatment of also complex chronic vaginal inflammation.

Since the formation of biofilms also occurs in many dermal fungal infections, emulsions according to this invention are also very well suited for the treatment of mycoses, especially *Candida mycoses*, but also infections with *malassezia*.

Accordingly, the emulsions according to the invention are preferably intended for use in the treatment of dermal and vaginal fungal infections, in particular for use in the topical treatment of vaginal fungal infections. In general, the emulsions according to the invention can be used in the treatment of infectious diseases, in particular of vaginal infections caused by *Candida albicans* or of vaginal mixed infections caused by *Candida albicans* and bacteria, such as *Enterobacter, E. coli, Klebsiella pneumoniae, Gardnerella vaginalis*, or *Prevotella* spp. A specific embodiment of the present invention lies in its application in the treatment of bacterial vaginosis. A further specific embodiment of the present invention lies in its application in the treatment of dermal and mucosal fungal and mixed infections, preferably of *Candida mycoses*, in particular vulvovaginal candidiasis, oropharyngeal candidiasis (oral thrush), nappy dermatitis (nappy rash), anal eczema, intertriginous eczema, and *Malassezia mycoses* (pityriasis versicolor).

Since in the case of chronic infections the inflammation of the epithelium may persist, the present invention also relates to emulsions which do not contain an antifungal or antimicrobial active substance. Due to their reliable release of the NSAID, which results from the special composition, these emulsions are very well suited for use in the aftercare of mucosal infections, especially vaginal inflammation. Such semi-solid emulsions are also very well suited for treating chronic inflammation of other causes, especially inflammation of mucosas and the immediately adjacent tissues. Examples of this can be found in the aftercare of chronic cystitis, atrophic vaginitis or inflammation of the anal mucosa. The emulsions according to the invention are therefore particularly suitable for use in the treatment of inflammation of the mucosas and mucosal infections, especially vaginal infections and vaginal inflammation, especially chronic inflammation and infections.

The invention will be explained in greater detail hereinafter by means of the following drawings and examples, to which it is not, however, restricted.

FIGURES

FIG. 1: Phase II clinical study. Pain diaries of patients with recurrent vulvovaginal candidiasis (RVVC) who were treated with emulsions according to the invention containing different concentrations of diclofenac Na (CP1: 0.2 wt. %, CP2: 0.3 wt. %, CP3: 0.4 wt. %) or with a control composition without diclofenac Na ("comparator") according to the invention. The intensity of pain was recorded by the patients at the time of recording on a pain scale from 0 to 10. The diagram shows the mean values of the treatment groups during the course of treatment. At CP 1, there is a rapid decrease in pain intensity, but the healing curve flattens out as soon as the daily dose is halved (from day 4). CP 2 shows an optimal healing process. Already on day 2 the pain level has decreased to 50% of the initial value.

EXAMPLES

Preliminary Remark

Changes in the preparation method and in the percentage composition of an oil-in-water mixture corresponding to base formulation A showed surprising changes in clinical efficacy away from the usual dose-effect relationships. The significantly improved or possibly also reduced efficacy can be derived from a particularly rapid onset of action (local pain relief) or a delay in the onset of action or the intensification of existing pain.

Example 1—Basic Formulation

TABLE 1

| Basic formulation A | |
|---|---|
| Composition of the emulsion | |
| Clotrimazole | 1.00 |
| Diclofenac Na | 0.20 |
| Sorbitan monostearate | 2.00 |
| Polysorbate 60 | 1.50 |
| Cetylpalmitate | 3.00 |
| 2-octyldodecanol | 13.50 |
| Cetostearyl alcohol | 10.00 |
| Benzyl alcohol | 1.00 |
| Purified water Ph. Eu. | 67.80 |
| Total | 100.00 |
| Ph | 7.8 |

If the concentration of the NSAID changes, it is exchanged in each case for purified water; the content of lipid components remains the same, unless otherwise stated. The clinical efficacy in the following preparations is related to a clinically effective basic formulation A.

Example 2: Variations of the pH Range and Clinical Efficacy

Changes with respect to preservatives are associated with changes in the pH value. The stated examples were prepared according to general preparation instructions 1. The adjustment of the pH value to achieve the optimum effect of the preservative in question was carried out by adding suitable buffer solutions by which the relevant amount of purified water had been replaced.

The pH value has a significant influence on the locally bioavailable amount of active substance by shifting the free active substance proportion compared to the proportion present as salt. Depending on the pKa values of the non-steroidal antiphlogistics used, this results, in accordance with the present invention, in a pH optimum of the combination preparations according to the invention.

TABLE 2 pH dependence of clinical efficacy

| Composition | Conc. wt. % | Conc. wt. % |
|---|---|---|
| Clotrimazole | 1 | 1 |
| Diclofenac Na | 0.25 | 0.25 |
| Sorbitan monostearate | 2 | 2 |
| Polysorbate 60 | 1.5 | 1.5 |
| Cetylpalmitate | 3 | 3 |
| 2-octyldodecanol | 13.5 | 13.5 |
| Cetylstearyl alcohol | 10 | 10 |
| Phenoxyethanol | 1 | 0 |
| Bronopol | 0.1 | 0 |
| Sorbic acid | 0 | 0.2 |
| Buffer solution | 0.2201 | 0.0874 |
| Purified water Ph. Eur. | 67.4299 | 68.4626 |
| Total | 100 | 100 |
| Ph | 7.5 | 5.6 |
| Clin. efficacy | conforms | reduced |
| Microbiol. stability | conforms | conforms |

Example 3: Influence of the Aqueous Phase/Oil Weight Ratio

Surprisingly, changes in viscosity show clear influences on clinical efficacy even with a small range of variation. The stated examples were prepared according to general preparation instructions 1 by varying the content of fatty components and the water content.

An increase in the water content and thus a decrease in viscosity leads to local irritation and reduced clinical efficacy through increased release and increased wetting of the mucosas.

TABLE 3

Influence of the aqueous phase/oil weight ratio on the clinical efficacy

| Phase | Fat component/ viscosity reduced | | Basic formulations | | Fat component/ viscosity increased | |
|---|---|---|---|---|---|---|
| Clotrimazole (oil) | 1 | 1.0 | 1.0 | 1.0 | 1.0 | 1.0 |
| Diclofenac Na (water) | 0.3 | 0.3 | 0.3 | 0.3 | 0.3 | 0.3 |
| Sorbitan monostearate (—) | 2.0 | 2.0 | 2.0 | 2.0 | 2.0 | 2.0 |
| Polysorbate 60 (—) | 1.5 | 1.5 | 1.5 | 1.5 | 1.5 | 1.5 |
| Cetylpalmitate (oil) | 3.0 | 3.0 | 3.0 | 3.0 | 3.0 | 3.0 |
| 2-octyldodecanol (oil) | 13.5 | 13.5 | 13.5 | 13.5 | 13.5 | 14.5 |
| Cetylstearyl alcohol (oil) | 7.5 | 5 | 10 | 10 | 14 | 16 |
| Benzyl alcohol (oil) | 1.0 | 1.0 | 1.0 | | 1.0 | 1.0 |
| Phenoxyethanol (oil) | | | | 1.0 | | |
| Propylene glycol (water) | | | | 7 | | |
| Water (water) | 70.2 | 72.7 | 67.75 | 60.7 | 63.7 | 60.7 |
| Total | 100 | 100 | 100 | 100 | 100 | 100 |
| Clinical efficacy | irritating | irritating | conforms | conforms | reduced | reduced |
| Water phase total | 70.5 | 73.0 | 68.0 | 68.0 | 64.0 | 61.0 |
| Fat phase total | 26 | 23.5 | 28.5 | 28.5 | 32.5 | 35.5 |
| aqueous phase/fat | 2.7 | 3.1 | 2.4 | 2.4 | 2.0 | 1.7 |

To calculate the weight ratio of the water phase to the oil phase, the individual proportions of the water and oil phases are added together as shown in the table. Since emulsifiers, for example sorbitan monostearate and polysorbate 60, are located at the interfaces between the two phases, they are not assigned to either the water or the oil phase.

If the ratio of the aqueous phase to the oil phase of the concentrated emulsion (i.e. the intermediate product of components A, B, J, C, E, G, H and half of K) of example 2 of WO 02/0768648 A2 is calculated, a ratio of 3.1 is obtained (oil phase: terbinafine, butylhydroxytoluene, benzyl alcohol, isopropyl myristate, total 11.52 g/100 g; water phase: diclofenac sodium and water, total 35.94 g/100 g; ratio 3.1). Such an emulsion therefore has a water-to-oil ratio outside the scope of the invention and would therefore not be suitable in the context of the present invention.

Alternatively, the weight ratio of the water phase to the oil phase could be calculated without including the substances dissolved in the phases (clotrimazole, diclofenac Na, benzyl alcohol, cetylstearyl alcohol). With this method of calculation, only water and propylene glycol would be attributed to the water phase in Table 3, and cetyl palmitate, 2-octyldodecanol and cetylstearyl alcohol to the oil phase. The water-to-oil ratios 2.7, 3.1, 2.4, 2.4, 2.0, 1.7 given in Table 3 would correspond to the values 2.9, 3.4, 2.6, 2.6, 2.1, 1.8 according to this calculation method. The range according to the invention of 2.0 to 2.7 would correspond to a range of 2.1 to 2.9 according to this calculation method.

In the context of the present invention, however, the calculation of the weight ratio of the water phase to the oil phase shall be carried out as shown in Table 3, i.e. including the substances dissolved in the phases.

Example 4: Variation of the Non-Steroidal Antiphlogistic

Instead of diclofenac, various other non-steroidal antiphlogistics were added to the basic formulation A and examined for their clinical efficacy.

TABLE 4

Variations of non-steroidal antiphlogistics

| Formulation no. | Non-steroidal antiphlogistic | Preparation | Preparation variant | Efficacy |
|---|---|---|---|---|
| 1.1 | Mefenamic acid | 1 g/100 g | Basic formulation A + mefenamic acid micronised | conforms |
| 1.2 | Indometacin | 0.15 g/100 g | Basic formulation A + indometacin micronised | conforms |
| 1.3 | Ibuprofen | 1 g/100 g | Basic formulation A + ibuprofen hydrogel | conforms |
| 1.4 | Ibuprofen | 0.5 g/100 g | Basic formulation A + ibuprofen hydrogel | conforms |
| 1.5 | Naproxen | 1 g/100 g | Basic formulation A + naproxen micronised | conforms |

Example 5: Optimum Concentration

According to the basic formulation A, emulsions with different concentrations of diclofenac Na were prepared and tested for their clinical efficacy.

TABLE 5

Dependence of clinical efficacy on the concentration of NSAIDS

| | Conc. wt. % | Conc. wt. % | Conc. wt. % | Conc. wt. % |
|---|---|---|---|---|
| Clotrimazole | 1 | 1 | 1 | 1 |
| Diclofenac Na | 0.1 | 0.25 | 0.5 | 0.75 |
| Sorbitan monostearate | 2 | 2 | 2 | 2 |
| Polysorbate 60 | 1.5 | 1.5 | 1.5 | 1.5 |
| Cetylpalmitate | 3 | 3 | 3 | 3 |
| 2-octyldodecanol | 13.5 | 13.5 | 13.5 | 13.5 |
| Cetylstearyl alcohol | 10 | 10 | 10 | 10 |
| Benzyl alcohol | 1 | 1 | 1 | 1 |
| Purified water Ph. Eur. | 67.9 | 67.75 | 67.5 | 67.25 |
| Total | 100 | 100 | 100 | 100 |
| Ph | 7.6 | 7.8 | 8.1 | 8.1 |
| Clin. efficacy | slightly reduced | conforms | conforms, slightly irritating | irritating to the mucosa |

Example 6: Variation of Preservatives and Microbiological Stability

The combined use of clotrimazole and NSAIDs changes both microbiological and chemical stability [Lit. Pharmacopoeia] compared to a comparable clotrimazole formulation due to the pH shifts in the emulsion system.

TABLE 6

Variants with different preservatives

| Composition | wt. % | wt. % | wt. % | wt. % | wt. % |
|---|---|---|---|---|---|
| Clotrimazole | 1 | 1 | 1 | 1 | 1 |
| Diclofenac Na | 0.4 | 0.3 | 0.3 | 0.25 | 0.25 |
| Sorbitan monostearate | 2 | 2 | 2 | 2 | 2 |
| Polysorbate 60 | 1.5 | 1.5 | 1.5 | 1.5 | 1.5 |
| Cetylpalmitate | 3 | 3 | 3 | 3 | 3 |
| 2-octyldodecanol | 13.5 | 13.5 | 13.5 | 13.5 | 13.5 |
| Cetylstearyl alcohol | 10 | 10 | 10 | 10 | 10 |
| Propylene glycol | | 7 | 5 | | |
| Phenoxyethanol | 4 | 1 | 1 | 1 | |
| Bronopol | | | | 0.1 | |
| Sorbic acid | | | | | 0.2 |

TABLE 6-continued

| Variants with different preservatives | | | | | |
|---|---|---|---|---|---|
| Composition | wt. % | wt. % | wt. % | wt. % | wt. % |
| Buffer solution | | | | 0.2201 | 0.0874 |
| Purified water Ph. Eur. | 64.6 | 60.7 | 62.7 | 67.4299 | 68.4626 |
| Total | 100 | 100 | 100 | 100 | 100 |
| Ph | 7.9 | 7.6 | 7.9 | 7.5 | 5.6 |
| Clin. efficacy | conforms | conforms | conforms | conforms | reduced |
| Microbiol. stability | conforms | conforms | conforms | conforms | conforms |

Example 7

Preparation of Basic Formulation A

General Preparation Instructions 1

The components sorbitan monostearate, polysorbate 60, cetyl palmitate, 2-octyldodecanol and cetostearyl alcohol are melted at a temperature of 70-75° C. Clotrimazole and then benzyl alcohol are added to the clear melt while stirring at a temperature of 60° C.-70° C. At the same time, diclofenac sodium is dissolved in purified water while heating. The aqueous solution is added to the oil phase while stirring and homogenised. Under slow cooling with further homogenisation of the w/o emulsion formed, a phase inversion takes place which results in a hydrophilic, homogeneous cream.

TABLE 8

| Formulations based on Formulation A, preparation instructions 1 | | |
|---|---|---|
| Constituents of the emulsion | | |
| Clotrimazole | 1.00 | 1.00 |
| Diclofenac Na | 0.20 | 0.30 |
| Sorbitan monostearate | 2.00 | 2.00 |
| Polysorbate 60 | 1.50 | 1.50 |
| Cetylpalmitate | 3.00 | 3.00 |
| 2-octyldodecanol | 13.50 | 13.50 |
| Cetostearyl alcohol | 10.00 | 10.00 |
| Benzyl alcohol | 1.00 | 1.00 |
| Purified water Ph. Eur. | 67.80 | 67.70 |
| | 100.00 | 100.00 |

The clinical efficacy of the formulations in Table 8 is identical.

General Preparation Instructions 2

The components sorbitan monostearate, polysorbate 60, cetyl palmitate, 2-octyldodecanol and cetostearyl alcohol are melted at a temperature of 70-75° C. Clotrimazole is added to the clear melt while stirring at a temperature of 60° C.-70° C. and melted. At the same time, diclofenac sodium is dissolved in purified water while heating. After addition of phenoxyethanol and, if necessary, propylene glycol, the aqueous solution is added to the oil phase at a temperature of 60° C.-70° C. while stirring and homogenised. With slow cooling and further homogenisation of the w/o emulsion initially formed, a phase inversion to an o/w emulsion takes place, resulting in a hydrophilic, homogeneous cream. (For clinical results see Table 6)

Instead of dissolving the NSAID in water, it can also be incorporated by stirring in an NSAID dissolved in a hydrogel or by stirring in the (micronised) NSAID as a solid during emulsion preparation.

Example 9: Preparation of Basic Formulation a by Incorporating the NSAID into the Oil Phase Creams with different concentrations of Diclofenac Na were prepared according to basic formulation A in accordance with general preparation instructions 2 and their clinical efficacy was tested. Purified water was exchanged for diclofenac Na; the content of the lipid components, the O/W emulsifier polysorbate 60 and the preservative benzyl alcohol was identical in the formulations.

General Preparation Instructions 3

The components sorbitan monostearate, polysorbate 60, cetyl palmitate, 2-octyldodecanol and cetostearyl alcohol are melted. Benzyl alcohol is added to the clear melt while stirring (lipid phase). Purified water is heated to boiling point and 70% of the required mass according to the formulation is added to the lipid phase while stirring (phase inversion and formation of an O/W pre-emulsion). About 30% of the pre-emulsion is removed from the vessel, and clotrimazole and diclofenac sodium are dispersed in it. The active substance-containing pre-emulsion is added to the active substance-free pre-emulsion in the vessel and filled up to the final mass with purified water (remaining 30%). The cream is stirred until room temperature is reached, and finally, for homogenisation, it is passed twice over a three roll mill (pH 6.99).

TABLE 9

| Formulations based on formulation A, preparation instructions 3. | | |
|---|---|---|
| Composition | | |
| Clotrimazole | 2.00 | 2.00 |
| Diclofenac Na | 0.10 | 0.20 |
| Sorbitan monostearate | 2.00 | 2.00 |
| Polysorbate 60 | 1.50 | 1.50 |
| Cetylpalmitate | 3.00 | 3.00 |
| 2-octyldodecanol | 13.50 | 13.50 |
| Cetostearyl alcohol | 10.00 | 10.00 |
| Benzyl alcohol | 1.00 | 1.00 |
| Purified water Ph. Eur. | 66.90 | 66.80 |
| | 100.00 | 100.00 |
| Clin. efficacy | reduced | reduced |

From the examples according to preparation instructions 3, a significant influence of the preparation process results, which must be designed in such a way that the non-steroidal antiphlogistic is incorporated via the aqueous phase and is predominantly present in the aqueous phase.

Example 10: Preparation of Basic Formulation A

Preparation of basic formulation A with incorporation of a non-steroidal antiphlogistic (diclofenac Na) according to general preparation instructions 4:

The components sorbitan monostearate, polysorbate 60, cetyl palmitate, 2-octyldodecanol and cetostearyl alcohol are melted. Benzyl alcohol is added to the clear melt while stirring (lipid phase). Purified water is heated to boiling point and 70% of the required mass according to the formulation is added to the lipid phase while stirring (phase inversion and formation of an O/W pre-emulsion). About 30% of the pre-emulsion is removed from the vessel, and clotrimazole is dispersed in it. The active substance-containing pre-emulsion is added to the active substance-free pre-emulsion in the vessel and filled up to the final mass with purified water (remaining 30%). The cream is stirred with the addition of micronised diclofenac sodium in several portions until room temperature is reached, and finally, for homogenisation, it is passed twice over a three roll mill.

Example 11: Phase II Clinical Study

The clinical efficacy of emulsions according to the invention for the treatment of chronic vaginal infections was investigated in a phase II clinical study.

In accordance with general preparation instructions 1, three emulsions according to the invention with different concentrations of diclofenac Na were prepared. An emulsion without NSAID was used as a control:

Emulsion CP1: 0.2 wt. % diclofenac Na
Emulsion CP2: 0.3 wt. % diclofenac Na
Emulsion CP3: 0.4 wt. % diclofenac Na
Emulsion Comparator: 0 wt. % diclofenac Na 31 patients with chronic recurrent vaginal infections (chronic recurrent vulvovaginal candidiasis, RVVC) were treated. Patients with clinical symptoms of at least moderate severity were enrolled in the study after positive detection of fungal infection. In the first 3 days, 2.5 ml of cream were administered intravaginally twice daily by means of an applicator, and in the following 3 days 2.5 ml of cream were applied once daily. After 7-10 days a check-up examination was performed.

Each of the three emulsions according to the invention led to a better healing success than the control, which did not contain NSAID. Emulsion 2, containing 0.3 wt. % diclofenac Na, proved to be particularly beneficial. A complete clinical cure (complete freedom from symptoms at check-up examination by the treating physician) was achieved in all patients in this group. In the control group only 40% of the patients were cured.

As a further clinical parameter—in addition to the healing effect—the development of pain in chronic patients (pain diary) was used. The intensity of pain was entered by the patients at the time of recording on a pain scale from 0 to 10. The mean values of the treatment groups during the course of treatment are shown in FIG. 1. With a constant concentration of the antimycotic, it was found that in the highest concentration of the NSAID (emulsion 3), the course of healing was better compared to the control, but the decrease in pain intensity showed no significant difference as compared to the control group. The optimal concentration (emulsion 2), at which all patients were cured, quickly led to a complete reduction in pain. The clear dose dependence was also evident in the patients with the lowest concentration (emulsion 1), where the pain decreased significantly until the dosage was changed from twice-a-day to a once-a-day dosage, whereupon the healing process slowed down accordingly (see FIG. 1).

Microbiological tests carried out in parallel showed that none of the patients were infected with resistant *candida* strains, but the majority of RVVC patients did not respond to antifungal therapy.

Accordingly, the invention relates to the following preferred embodiments:

1. An emulsion with an aqueous phase and an oil phase, containing an NSAID, characterised in that (a) the NSAID in the aqueous phase is in a concentration range that corresponds to half to a tenth of the standard concentration for these active substances, in that (b) the weight ratio of the water phase to the oil phase in this emulsion is between the values 2.0 and 2.7, and in that (c) the pH value of the emulsion is not less than the value 6.5 and not more than 8.5, preferably in the range 7.0 to 8.0.

2. An emulsion with an aqueous phase and an oil phase, containing an antimycotic and an NSAID, characterised in that (a) the NSAID in the aqueous phase is in a concentration range that corresponds to half to a tenth of the standard concentration for these active substances, in that (b) the weight ratio of the water phase to the oil phase in this emulsion is between the values 2.0 and 2.7, and in that (c) the pH value of the emulsion is not less than the value 6.5 and not more than 8.5, preferably in the range 7.0 to 8.0.

3. An emulsion according to embodiment 1 or 2, characterised in that the weight ratio of the water phase to the oil phase in this emulsion is between the values 2.1 and 2.6, preferably between the values 2.2 and 2.55.

4. An emulsion according to one of the embodiments 1 to 3, characterised in that the pH value of the emulsion is in the range 7.0 to 8.5, preferably in the range 7.5 to 8.0

5. An emulsion according to one of embodiments 1 to 4, characterised in that it is in the form of a salve or a cream.

6. An emulsion according to one of embodiments 1 to 5, characterised in that the emulsion is semi-solid.

7. An emulsion according to one of embodiments 1 to 6, characterised in that the antimycotic is nystatin, ciclopirox or ciclopiroxolamine, or an antimycotic from the group of azoles, preferably clotrimazole, fluconazole, miconazole, itraconazole, tioconazole, voriconazole, bifonazole, econazole, isoconazole, fenticonazole, sertaconazole, ketoconazole, posaconazole, quilseconazole, oteseconazole (VT-1161) or ibrexafungerp (SCY-078).

8. An emulsion according to one of embodiments 1 to 7, characterised in that the antimycotic is clotrimazole.

9. An emulsion according to one of embodiments 1 to 8, characterised in that the NSAID is diclofenac, preferably in a concentration of 0.2 to 0.5 weight percent, ibuprofen, preferably in a concentration of 0.5 to 2.5 weight percent, bufexamac, dexibuprofen, flurbiprofen, ketoprofen, piroxicam, meloxicam, lornoxicam, flufenamic acid, mefenamic acid, indometacin, preferably in a concentration of 0.1 to 0.4 weight percent, or naproxen, preferably in a concentration of 0.5 to 2.5 weight percent.

10. An emulsion according to one of embodiments 1 to 9, characterised in that the NSAID is diclofenac and this is contained in a concentration range of 0.2-0.4 weight percent of the emulsion.

11. An emulsion according to one of embodiments 1 to 10, in which a preservative active in the pH range of the emulsion is contained.

12. An emulsion according to embodiment 11, in which the preservative is phenoxyethanol or propylene glycol or a combination of the two.

13. An emulsion according to embodiment 11, in which the preservative is dequalinium chloride.

14. An emulsion according to one of embodiments 1 to 13, characterised in that it further contains an antibiotic which acts against bacterial germs.

15. An emulsion according to embodiment 14, characterised in that the antibiotic is phosphomycin, clindamycin, metronidazole, nitrofurantoin, nitrofurazone, nitrofurantoin, nifuratel, nifuroxacin, nitroxolin, trimethoprim, sulfadiazine, or cotrimoxazole.

16. An emulsion according to one of embodiments 1 to 15, characterised in that it further contains an antiseptic, preferably in an amount sufficient for an acute antimicrobial effect.

17. An emulsion according to embodiment 16, characterised in that the antiseptic is a quaternary ammonium salt.

18. An emulsion according to embodiment 16 or 17, characterised in that the antiseptic is selected from the group consisting of: benzalkonium chloride, preferably in a concentration of at least 0.2 weight percent; dequalinium chloride, preferably in a concentration of at least 0.2 weight percent; and phenoxyethanol, preferably in a concentration of at least 2 weight percent.

19. An emulsion according to one of embodiments 1 to 18 for use in the treatment of dermal and vaginal fungal infections.

20. An emulsion according to one of embodiments 1 to 19 for use in the topical treatment of vaginal fungal infections.

21. Emulsion according to one of embodiments 1 to 20 for use in the treatment of chronic infections of the urogenital tract.

22. Emulsion according to one of embodiments 1 to 21 for use in the treatment of chronic vaginal fungal infections.

23. Emulsion according to one of embodiments 1 to 22 for use in the treatment of infectious diseases, in particular vaginal infections by *Candida albicans*.

24. Emulsion according to embodiments 1 to 23 for use in the treatment of infectious diseases, in particular mixed vaginal infections by *Candida albicans* and bacteria such as *Enterobacter, E. coli, Klebsiella pneumoniae, Gardnerella vaginalis*, and *Prevotella* spp.

25. Emulsion according to one of embodiments 1 to 24 for use in the treatment of bacterial vaginosis.

26. Emulsion according to embodiments 1 to 25 for use in the treatment of dermal or mucosal fungal infections, preferably of *Candida mycoses*, in particular vulvovaginal candidiasis, oropharyngeal candidiasis (oral thrush), nappy dermatitis (nappy rash), anal eczema, intertriginous eczema, and *Malassezia mycoses*.

27. Emulsion according to one of embodiments 1 to 26 for use in the treatment of mucosal inflammation, in particular chronic mucosal inflammation.

28. Emulsion according to one of embodiments 1 to 27 for use in the treatment of mucosal infections, in particular chronic mucosal infections.

29. Emulsion according to one of embodiments 1 to 28 for use in the post-treatment of mucosal infections, in particular vaginal inflammation.

30. Emulsion for use according to embodiment 29, characterised in that the vaginal inflammation are chronic.

31. Emulsion according to one of embodiments 1 to 30 for use in the treatment of inflammation of mucosas and the immediately adjacent tissues.

32. Emulsion according to one of embodiments 1 to 31 for use in the post-treatment of chronic cystitis.

33. Emulsion according to one of embodiments 1 to 32 for use in the treatment of atrophic vaginitis.

34. Emulsion according to one of embodiments 1 to 33 for use in the treatment of inflammation of the anal mucosa.

35. A process for preparing an emulsion according to one of embodiments 1 to 34, characterised in that, during preparation of the emulsion, the NSAID is introduced via the aqueous phase.

36. A process for preparing an emulsion according to one of embodiments 1 to 35, characterised in that the NSAID is introduced as a finely crystalline or micronised salt into the emulsion containing the antimycotic.

37. A process for preparing an emulsion according to one of embodiments 1 to 36, characterised in that the NSAID is introduced via a hydrogel into the emulsion containing the antimycotic.

38. A process for preparing an emulsion according to one of embodiments 1 to 37, in which the substances are added in such a way that a therapeutically effective antibacterial effect is obtained.

The invention claimed is:

1. An emulsion with an aqueous phase and an oil phase, comprising:
   an antimycotic and
   an NSAID,
   wherein (a) the NSAID is diclofenac in a concentration of 0.1 to 0.5 weight percent, indometacin in a concentration of 0.1 to 0.4 weight percent, naproxen in a concentration of 1 to 5 weight percent, ibuprofen in a concentration of 0.5 to 2.5 weight percent, dexibuprofen in a concentration of 0.25 to 1.25 weight percent, ketoprofen in a concentration of 0.25 to 1.25 weight percent, mefenamic acid in a concentration of 0.5 to 4 weight percent, or lornoxicam in a concentration of 0.02 to 0.04 weight percent,
   the NSAID is present in salt form; while (b) a weight ratio of the aqueous phase to the oil phase in the emulsion is between 2.0 and 2.7, and (c) a pH value of the emulsion is not less than 6.5 and not more than 8.5.

2. The emulsion according to claim 1, wherein the emulsion is in the form of a salve or a cream.

3. The emulsion according to claim 1, wherein the emulsion is semi- solid.

4. The emulsion according to claim 1, wherein the antimycotic is nystatin, ciclopirox or ciclopiroxolamine, or an antimycotic from a group of azoles.

5. The emulsion according to claim 1, wherein the antimycotic is clotrimazole.

6. The emulsion according to claim 1, wherein the NSAID is diclofenac and is contained in a concentration range of 0.2-0.4 weight percent of the emulsion.

7. The emulsion according to claim 1, further comprising a preservative active in the pH range of the emulsion.

8. The emulsion according to claim 7, wherein the preservative is phenoxyethanol, propylene glycol or a combination thereof.

9. The emulsion according to claim 7, wherein the preservative is dequalinium chloride.

10. The emulsion according to claim 1, further comprising an antibiotic which acts against bacterial germs.

11. The emulsion according to claim 1, further comprising an antiseptic.

12. The emulsion according to claim 11, wherein the antiseptic is selected from the group consisting of benzalkonium chloride; dequalinium chloride; and phenoxyethanol.

13. A method for treatment of a vaginal fungal infection, the method comprising:
   applying the emulsion according to claim 1 to a subject in need thereof.

14. The method according to claim 13, wherein the treatment is a topical treatment.

15. The method according to claim 13, wherein the vaginal fungal infection is a mixed vaginal infection by Candida albicans and bacteria.

16. The method according to claim 13, wherein the vaginal fungal infection is a candida mycosis.

17. A process for preparing the emulsion according to claim 1, the process comprising:
   introducing the NSAID into the aqueous phase.

18. A process for preparing the emulsion according to claim 1, the process comprising:
   introducing the N SAID as a finely crystalline or micronised salt into an emulsion comprising the antimycotic.

19. A process for preparing the emulsion according to claim 1, the process comprising:
   introducing the NSAID via a hydrogel into an emulsion comprising the antimycotic.

20. A process for preparing the emulsion according to claim 11, the process comprising:
   adding substances in such a way that a therapeutically effective antibacterial effect is obtained.

* * * * *